United States Patent [19]

Reutelingsperger

[11] Patent Number: 5,066,788

[45] Date of Patent: Nov. 19, 1991

[54] BLOOD COAGULATION INHIBITING PROTEINS, PROCESSES FOR PREPARING THEM AND THEIR USES

[75] Inventor: Christian M. Reutelingsperger, Maastricht, Denmark

[73] Assignee: Boehringer Ingelheim International GmbH, Fed. Rep. of Germany

[21] Appl. No.: 447,065

[22] Filed: Dec. 7, 1989

Related U.S. Application Data

[60] Continuation of Ser. No. 123,970, Nov. 23, 1987, which is a division of Ser. No. 779,287, Nov. 23, 1985, Pat. No. 4,736,018.

[30] Foreign Application Priority Data

Sep. 21, 1984 [NL] Netherlands .......................... 8402904
Mar. 4, 1985 [NL] Netherlands .......................... 8500601

[51] Int. Cl.$^5$ ...................... C07K 15/06; A61K 37/02
[52] U.S. Cl. ..................................... 530/381; 530/412; 530/413; 530/416; 530/420; 530/827
[58] Field of Search ............... 530/380, 381, 412, 413, 530/416, 420, 827, 829

[56] References Cited

U.S. PATENT DOCUMENTS

| | | | |
|---|---|---|---|
| 4,732,891 | 3/1988 | Maki et al. | 530/350 |
| 4,746,731 | 5/1988 | Bohn et al. | 530/350 |
| 4,748,156 | 5/1988 | Aoki et al. | 530/350 |

*Primary Examiner*—Nathan M. Nutter
*Attorney, Agent, or Firm*—Sterne, Kessler, Goldstein & Fox

[57] ABSTRACT

This invention discloses proteins which inhibit the coagulation of the blood, processes for preparing these proteins, and the use thereof.

1 Claim, 12 Drawing Sheets

94k
67k
43k

30k

20k 1    2 3 4 5 6

70,000 daltons →

34,000 daltons →
32,000 daltons →

1 2   3   4 5 6

BLOOD COAGULATION INHIBITING PROTEINS, PROCESSES FOR PREPARING THEM AND THEIR USES

This application is a continuation of U.S. patent application Ser. No. 07/123,970 (filed Nov. 30, 1987), allowed, which application is a division of U.S. patent application Ser. No. 06/779,287 (filed Nov. 23, 1985) and now U.S. Pat. No. 4,736,018.

BACKGROUND OF THE INVENTION

1. Field of the Invention

This invention relates to proteins which inhibit the coagulation of the blood, processes for preparing these proteins, and their use.

2. Description of the Background Art

Anti-coagulant proteins, which are present in most mammals, can be divided into three groups based on their different mechanisms of activity.

One group of proteins form a complex with a coagulation factor and thereby render the coagulation factor inactive. Proteins in this category include antithrombin III (*Thromb. Res.*, 5:,439-452 (1974)), alpha$_1$-protease inhibitor (*Ann. Rev. Biochem.*, 52:655-709 (1983)), alpha$_2$-macroglobulin (*Ann. Rev Biochem.*, 52: 655-709 (1983)), C$_1$-inhibitor (*Biochemistry* 20: 2738-2743 (1981)), and protease nexin (*J. Biol. Chem.*, 258: 10439-10444 (1983)).

A second group of proteins act proteolytically on a coagulating factor and thereby inactivate it. The only protein of this kind that has been described is protein C (*J. Biol. Chem.*, 251: 355-363 (1976)).

The third category to which anti-coagulant proteins can be grouped are those which screen and/or hydrolyze the negatively charged phospholipids so that the phospholipid-dependent reactions of the blood coagulation mechanism are inhibited. Thus far, only phospholipases isolated from various types of snake venom have been described as having this mode of action (*Eur. J. Biochem.*, 112: 25-32 (1980)).

In recent years, the step-wise coagulation system has been investigated thoroughly. It is understood to be an intensifying multi-stage system of different interconnected proteolytic reactions in which an enzyme converts a zymogen into the active form (cf. Jackson, C. M. and Nemerson, Y., *Ann. Rev. Biochem.*, 49: 765-811 (1980)). The speed of this reaction is decisively increased by the presence of phospholipids and other cofactors such as factor $V_a$ and factor $VIII_a$. In vivo, the procoagulation reactions are regulated by a variety of inhibitory mechanisms which prevent an explosively thrombotic trauma after slight activation of the coagulation cascade.

The mechanisms by which the anti-coagulation proteins of these three groups act have been described (Rosenberg, R. D. and Rosenberg, J. S., *J. Clin. Invest.*, 74: 1-6 (1984)).

In Group 1, serine-protease factor $X_a$ and thrombin are inactivated as a result of their binding to antithrombin III or to the antithrombin/heparin complex. Both the prothrombin activation and also the formation of fibrin can be inhibited in this way. In addition to antithrombin III, there are also various other plasma-protease inhibitors such as alpha2-macroglobulin and antitrypsin, the activity of which is dependent on time.

In Group 2, the discovery of protein C led to another anti-coagulation mechanism. Once protein C is activated, it acts as an anti-coagulant by selective proteolysis of the protein cofactors $V_a$ and $VIII_a$, by which prothrombinase and the enzyme which converts factor X are deactivated.

In Group 3, plasmin cleaves monomeric fibrin 1, a product of the effect of thrombin on fibrinogen, thereby preventing the formation of an insoluble fibrin (Nossel, H. L., *Nature,* 291: 165-167 (1981)).

Of the above-mentioned native proteins involved in the coagulation process, at present only antithrombin III is clinically used. However, the increase in the tendency to bleed when this protein is administered has proven to be a serious disadvantage.

All the agents previously used as anticoagulants, whether native to the body or synthetic, in some way render the coagulation factors ineffective and thereby lead to side effects which have a disadvantageous effect on the coagulation process.

SUMMARY OF THE INVENTION

It has been found possible to isolate native proteins which have blood coagulation-inhibiting properties, but do not increase the risk of bleeding. These proteins lose their inhibiting properties in the event of major bleeding, so that the normal coagulation processes can proceed without disruption and there is no danger of bleeding to death.

The present invention thus relates to anti-coagulant proteins, hereinafter referred to as VAC (Vascular Anti-Coagulant), which do not inactivate the coagulation factors. These proteins are capable of inhibiting the coagulation induced by a vascular procoagulant or by the factor $X_a$, but do not inhibit the coagulation induced by thrombin. In addition, they do not inhibit the biological and amidolytic activity of factors $X_a$ and $II_a$.

Lane 1: reduced reference proteins; Lane 2: supernatant of VAC preparation centrifuged in the absence of liposomes; Lane 3: supernatant of VAC preparation centrifuged in the presence of liposomes; Lane 4: supernatant of VAC preparation centrifuged in the presence of liposomes and $Ca^{++}$; Lane 5: supernatant from liposome precipitate of Lane 4 resuspended in TBS (10 mM EDTA) and centrifuged.

Figure 5:
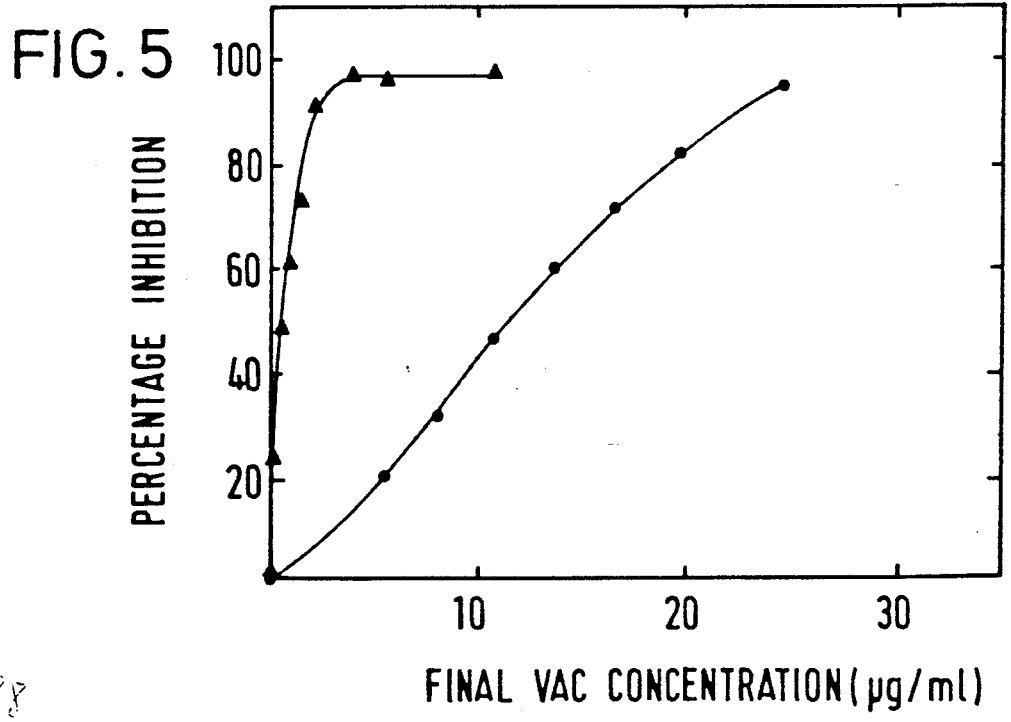

FIG. 5: Effect of VAC Concentration on Inhibition (%) of Thrombin Formation. The concentrations of VAC mentioned are the final concentrations present in the test systems. The thrombin formation was measured in 1 μM prothrombin, 10 nM factor $X_a$ and 0.5 M (▲—▲) or 5.0M (●—●) phospholipid membrane (PC/PS; 4:1, mol/mol) in 10 mM TBSA with $CaCl_2$. The reaction mixture was stirred with the specified quantities of VAC (Specific activity: 1300 units/mg) for 3 minutes at 37° C. without prothrombin. By adding prothrombin to the mixture, as in Example 1, the thrombin formation was initiated and the speed measured. The speed of thrombin formation in the absence of VAC was 3.3 nM $II_a$/min. (▲—▲) or 10.9 nM $II_a$/min. (●—●).

Figure 6:
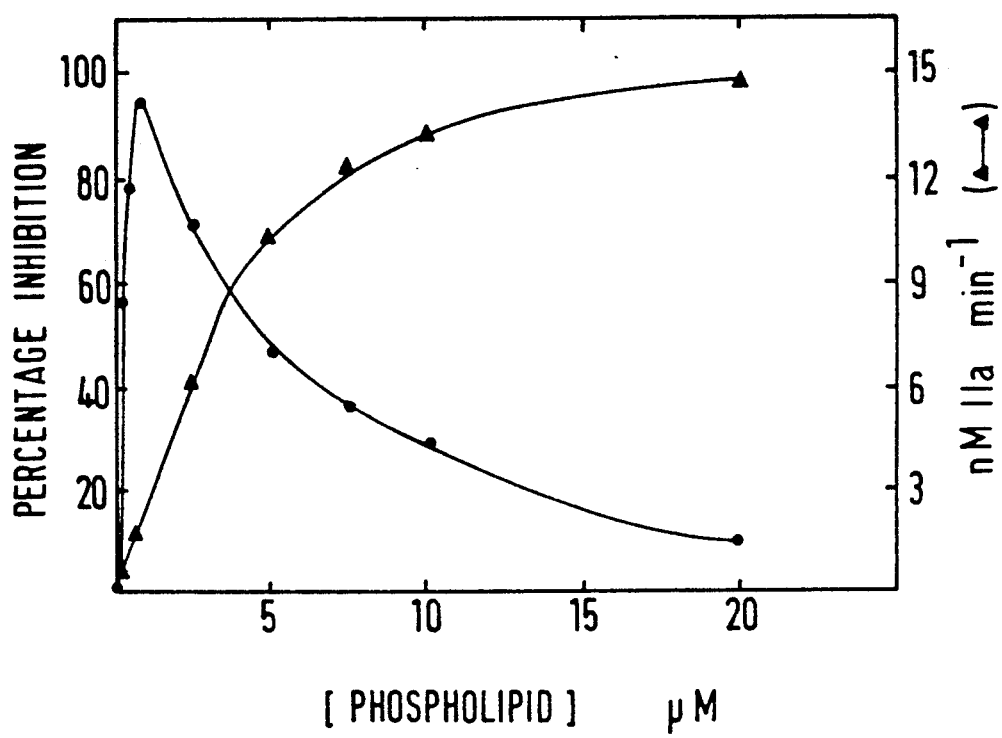

FIG. 6: Effect of Phospholipid Concentration on Inhibition (%) of Thrombin Formation by VAC. Thrombin formation was measured at 1 μm prothrombin, 10 nM factor $X_a$, 10.7 μg/ml VAC (Specific activity: 1300 units/mg) and at various concentrations of phospholipid membrane (PC/PS; 4:1, mol/mol) in TBSA. Factor $X_a$, VAC and phospholipid were stirred in TBSA for 3 minutes at 37° C. The thrombin formation was initiated by adding prothrombin to the reaction mixture. The rate of thrombin formation was measured as described in Example 1. The percent inhibition of thrombin formation (■—■) was measured for each phospholipid concentration with the corresponding rate of thrombin formation in the absence of VAC (▲—▲).

Figure 7:
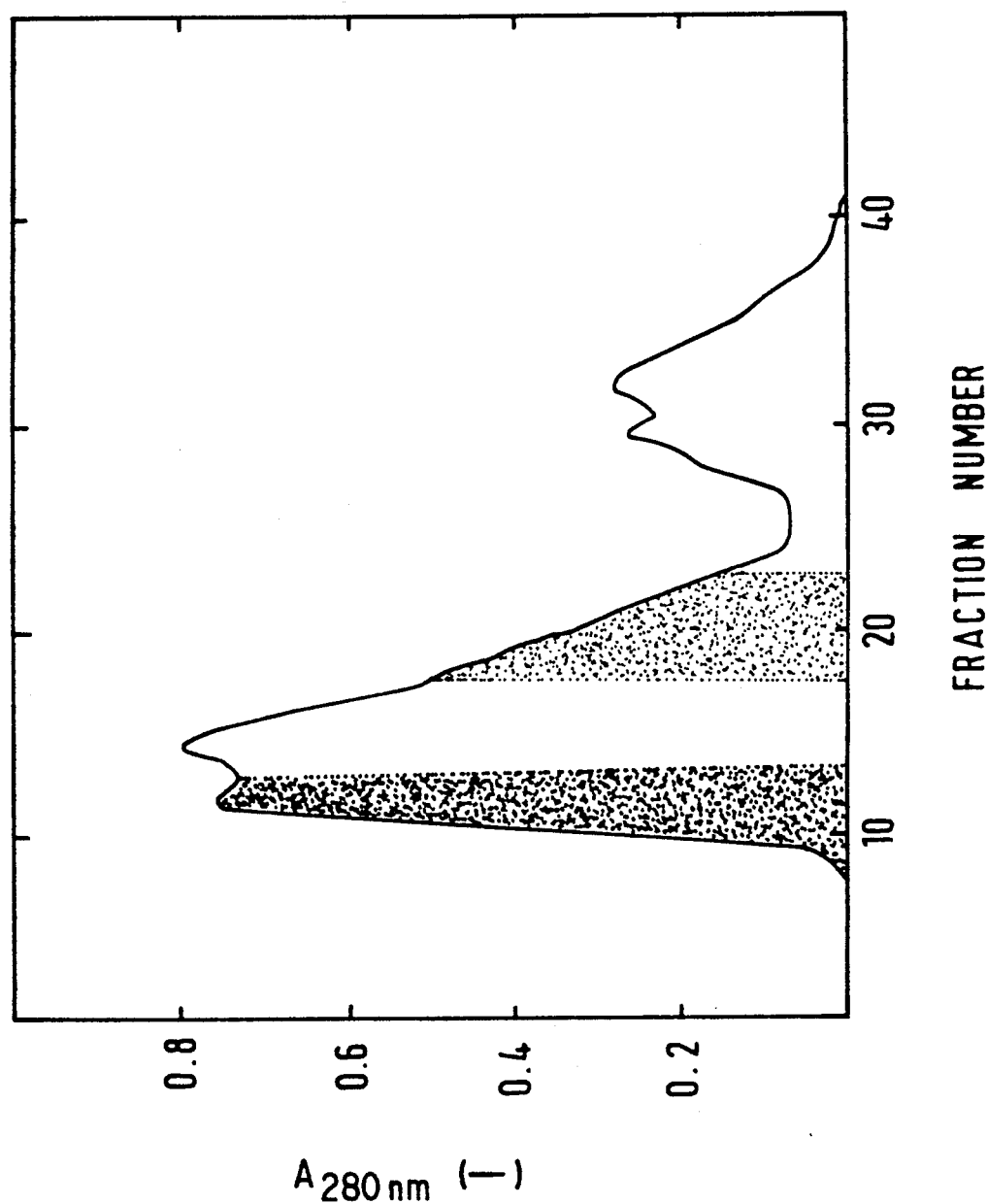

FIG. 7: Gel Filtration of the 10,000×g Supernatant of an Umbilical Cord Artery Homogenate on Sephadex G-100. 2 ml of the 10,000×g supernatant of a homogenized umbilical cord was loaded on a Sephadex G-100 column (1.5×80 cm), which was pre-equilibrated with TBS. The column was eluted with TBS. Aliquots of the resulting fractions were tested in the MPTT. Certain fractions (■) express a procoagulant activity and initiated coagulation in the MPTT without the addition of HTP, factor $X_a$, or thrombin. Other distinct fractions (◻) prolong clotting time in the MPTT, using HTP to initiate coagulation. These fractions were pooled and further fractionated.

Figure 8:
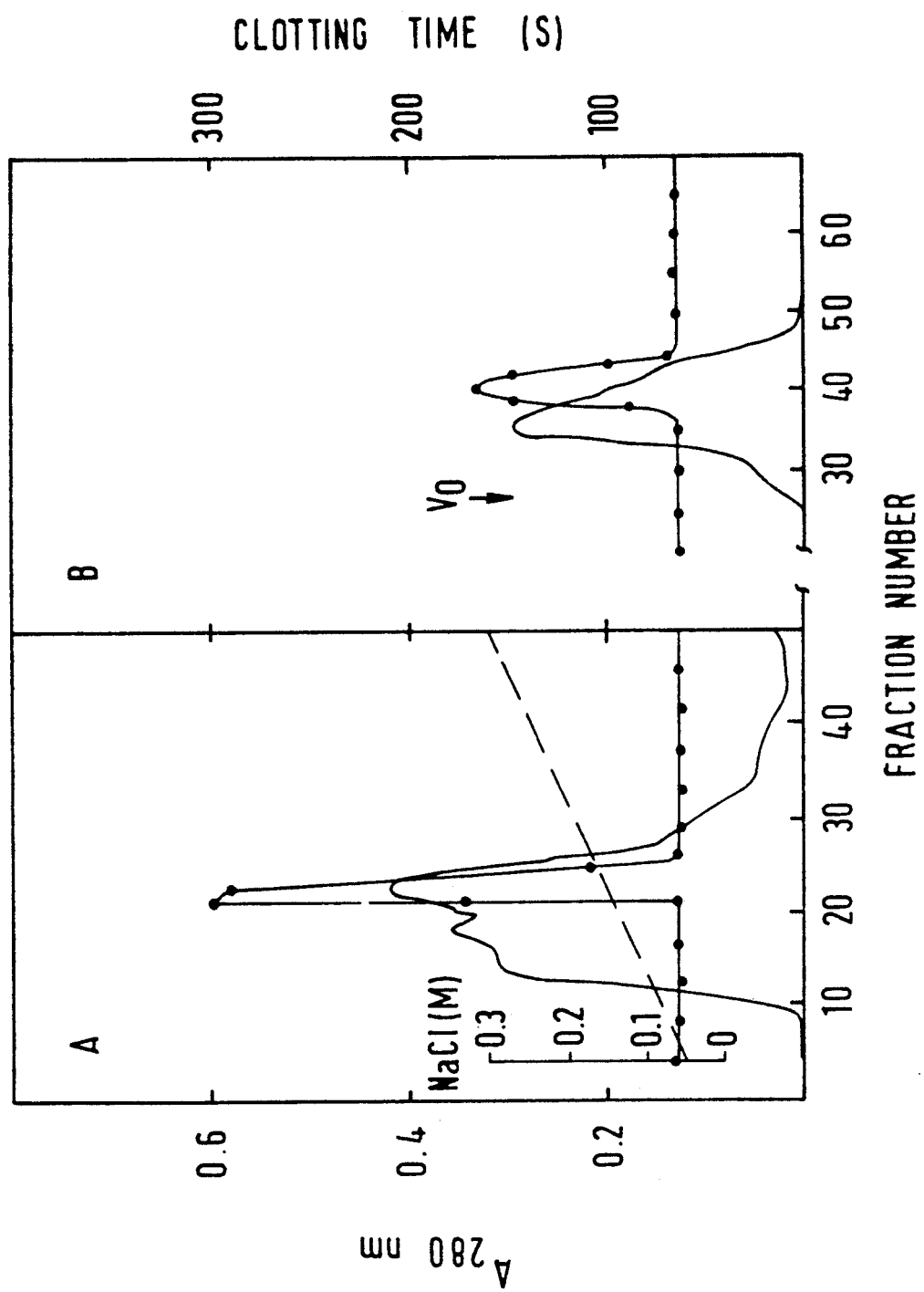

FIG. 8: Chromtoqraphy of the Anti-Coagulant on DEAE-Sephacel (A) and Sephadex G-75 (B). The pool, containing the anti-coagulant, from the Sephadex G-100 column was applied to DEAE-Sephacel. Elution was performed with a 200 ml linear gradient of 50–300 mM NaCl (-). Fractions (4 ml) were collected. $A_{280}$ was measured for each fraction (—) and anti-coagulant activity assayed in the MPTT using HTP (final concentration: 95 μg protein/ml) as initiator of coagulation (●). The fractions with anti-coagulant activity were pooled, concentrated, and subsequently applied to Sephadex G-75 (B). Fractions (2 ml) were collected. Each fraction was measured for $A_{280}$ (—) and anti-coagulant activity (●). $V_o$ represents the void volume of the column.

Figure 9:
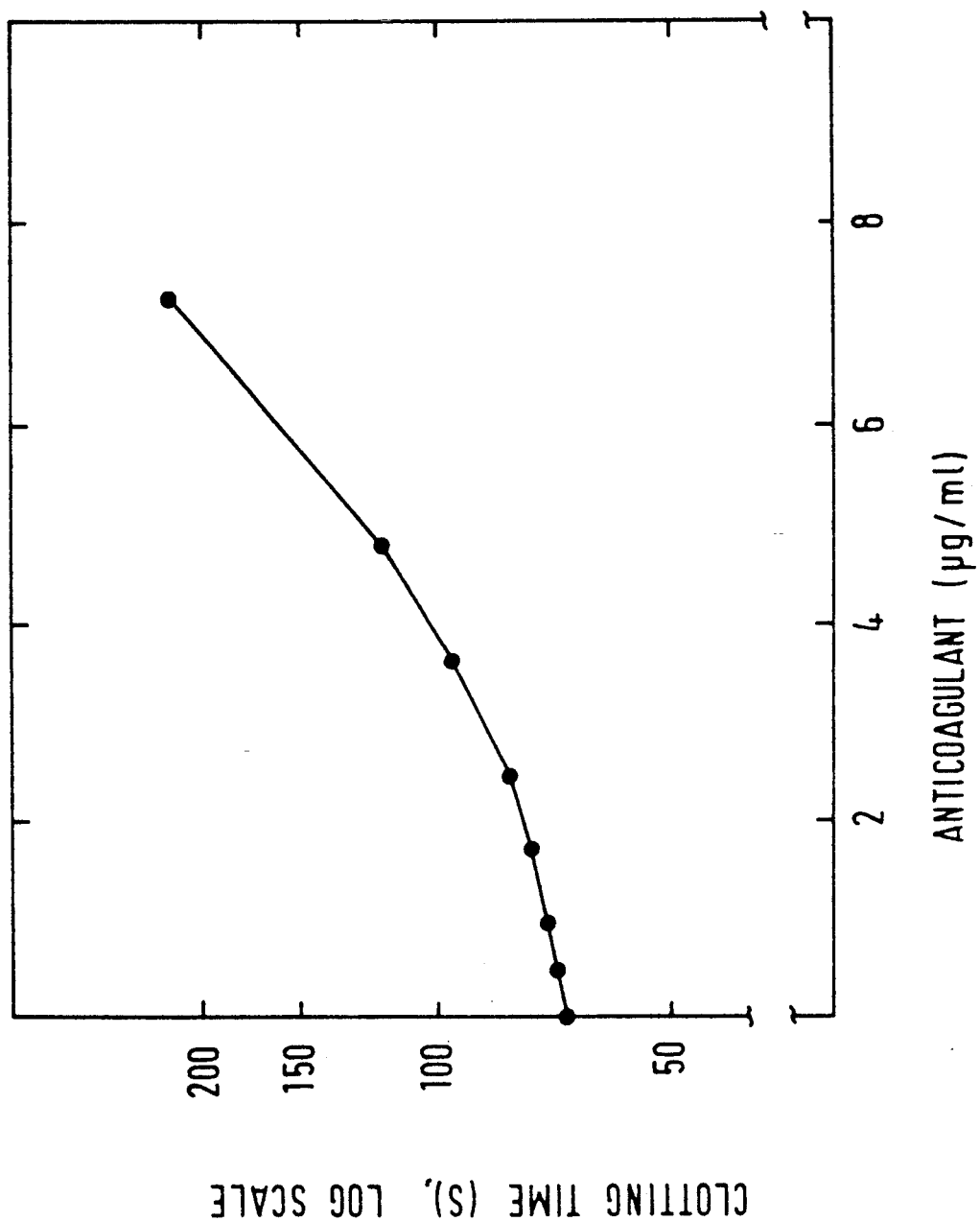

FIG. 9: Dose Response of the Anti-Coagulant in the MPTT. Varying amounts of the anti-coagulant were added to the MPTT. Coagulation was initiated with HTP (final concentration: 95 μg protein/ml). Control clotting time was 65 s.

Figure 10:
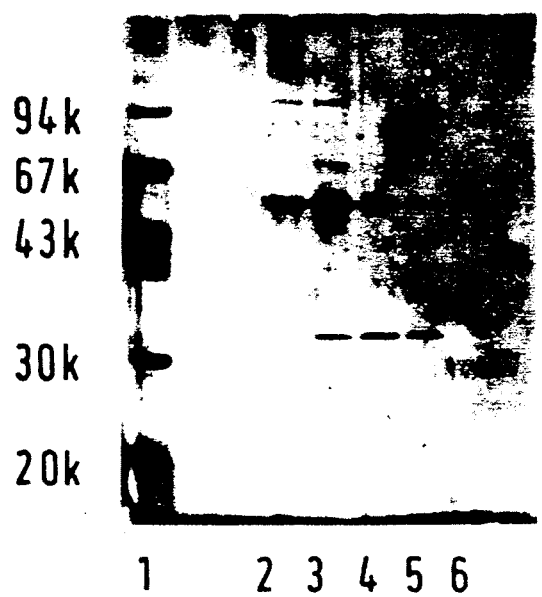

FIG. 10: Gel Electrophoresis of Several Fractions of the G-75 Eluant. Several fractions of the G-75 eluant were analyzed by SDS-PAGE. The gels were silver-stained according to Merril et al, *Electrophoresis J.,* 3: 17–23 (1982)). Lane 1: reduced low molecular weight standards; Lanes 2–6: unreduced aliquots of the G-75 fractions numbers 35, 39, 41, 43 and 50, respectively.

Figure 11:
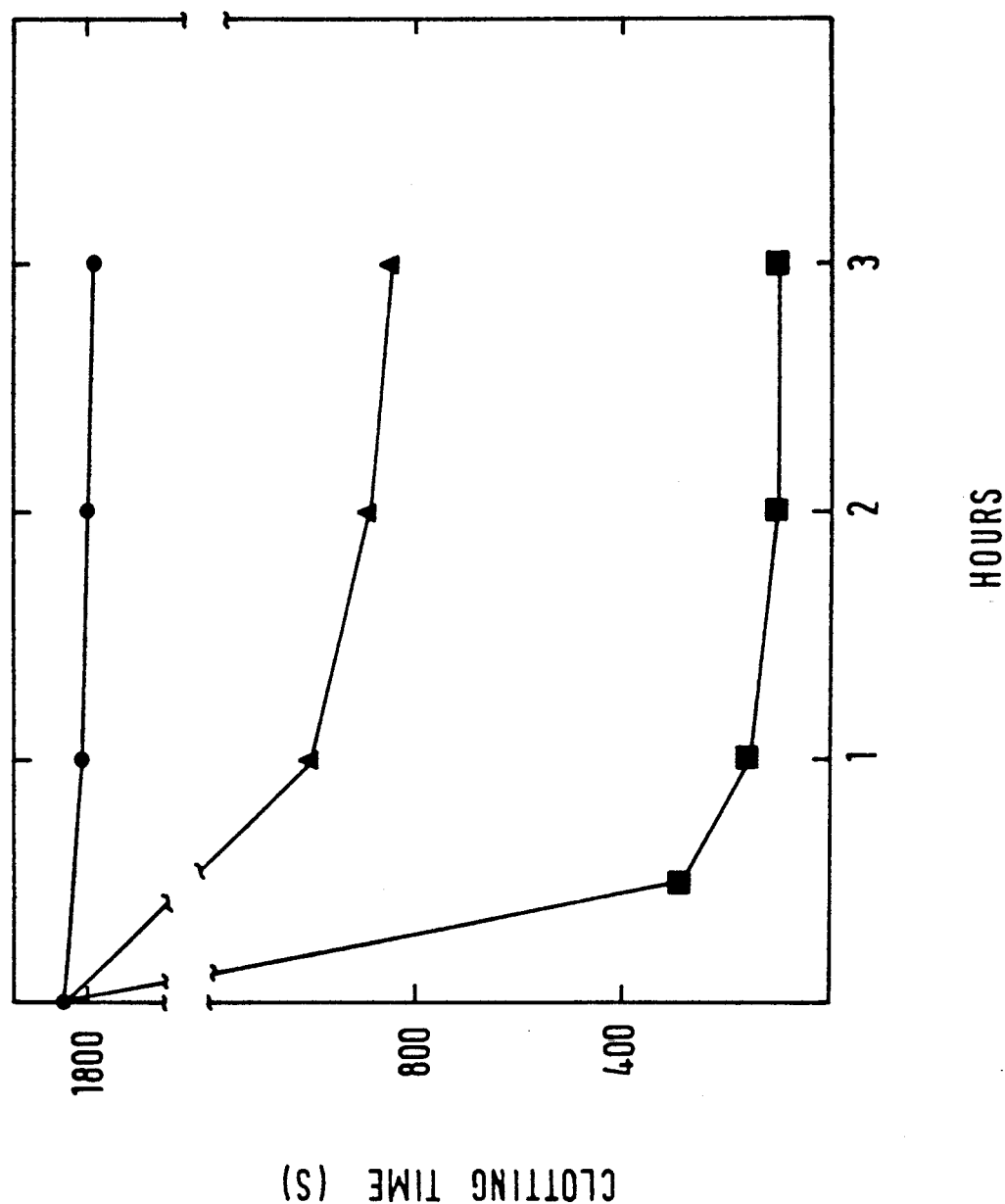

FIG. 11: The Effect of Proteolytic Enzymes on the Activity of the Anti-Coagulant. The anti-coagulant was incubated at 37° C. with protease type I (■, final concentration: 0.11 units/ml), trypsin (▲, final concentration: 88 BAEE units/ml) and without proteolytic enzymes (●). At the times indicated, 5 μl containing 6 μg protein of the anti-coagulant was removed from the reaction mixture and added to the MPTT. Clotting was initiated with HTP (final concentration: 18 ug protein/ml). Control clotting time was 110 s. The units given in this legend for the proteolytic enzymes are calculated from the values supplied by the manufacturer.

Figure 12:
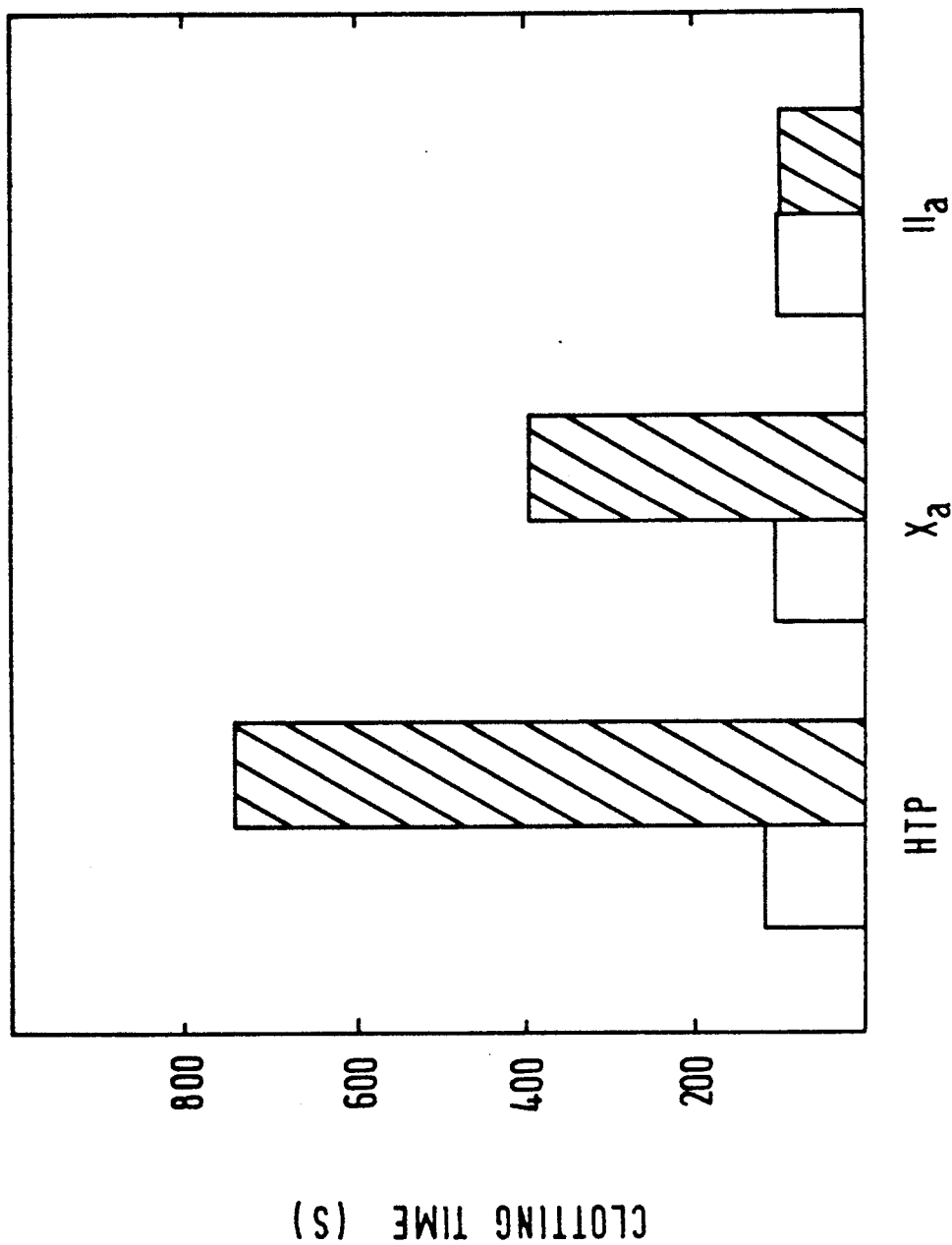

FIG. 12: Effect of Vascular Anti-Coagulant on the Clotting Times, -Induced in the MPTT by Either HTP, Factor $X_a$, or thrombin. The concentrations of the coagulation initiators (HTP: 18 μg protein/ml, 1.5 nM factor $X_a$, or 0.4 nM thrombin) were chosen to give control clotting times of about 110 seconds (open bars). When factor $X_a$ was used, phospholipid vesicles (final concentration 10 μM), composed of $Ole_2Gro$-P-Ser/$Ole_2Gro$-P-Cho (molar ratio, 20:80) were added to the reaction mixture. Clotting times induced by the indicated agents in the presence of 3.5 μg anti-coagulant protein are shown by the shaded bars.

Figure 13:
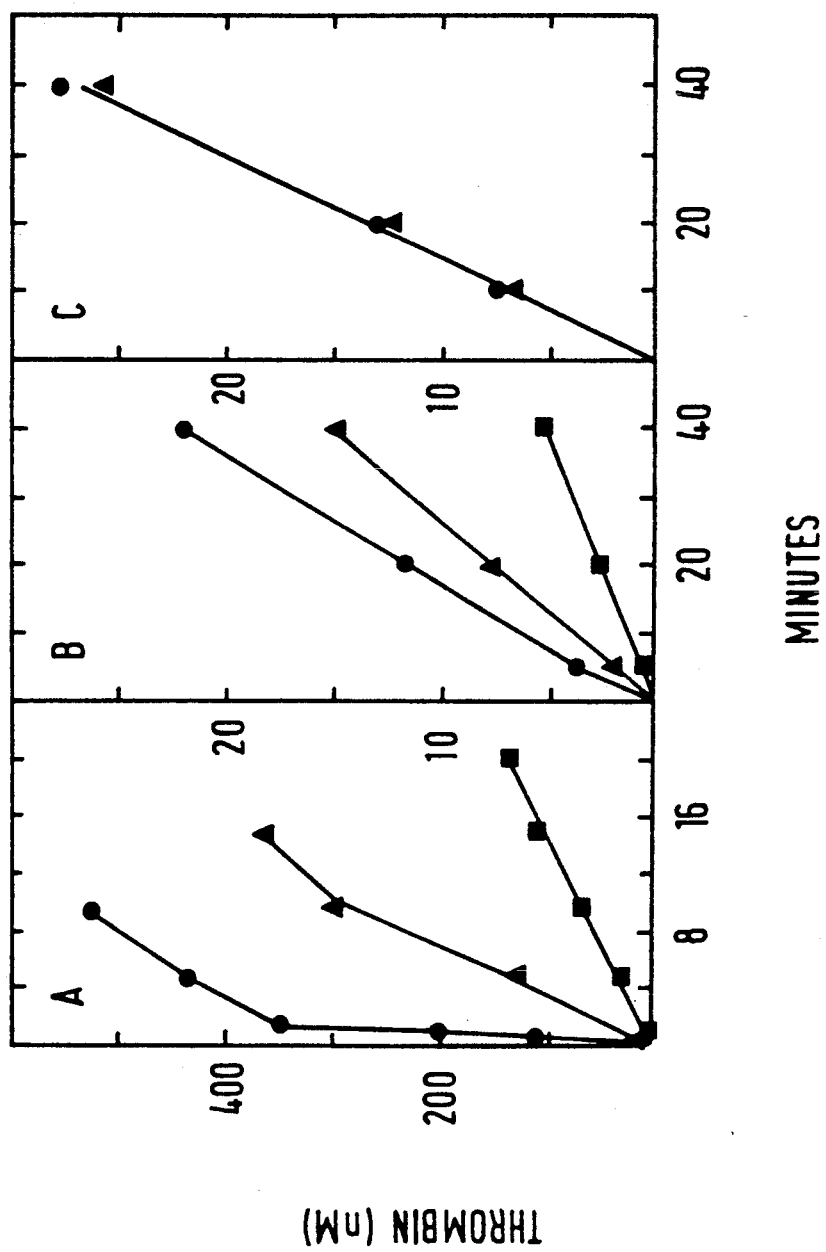

FIG. 13: Effect of the Anti-Coagulant on Prothrombin Activation by ($X_a$, $V_a$, phospholipid, $Ca^{2+}$), ($X_a$, phospholipid, $Ca^{2+}$), ($X_a$, $Ca^{2+}$). The reaction mixtures contained: (A) 1 μM prothrombin, 0.3 nM $X_a$, 0.6 nM $V_a$, 0.5 μM phospholipid and 10 mM $CaCl_2$ with 12.0 μg/ml anti-coagulant (■), 4.8 μg/ml anticoagulant (▲), and 0.0 anticoagulant (◆); (B) 1 μM prothrombin, 10 nM $X_a$, 0.5 μM phospholipid, and 10 mM $CaCl_2$ with 2.4 μg/ml anti-coagulant (■), 0.48 μg/ml anti- coagulant (▲), and 0.0 anti-coagulant (●); (C) 1 μM prothrombin, 75 nM $X_a$, and 10 mM $CaCl_2$ with 120 μg/ml anti-coagulant (▲), and 0.0 anti-coagulant (●). At times indicated, samples were removed and thrombin was determined.

Figure 14:
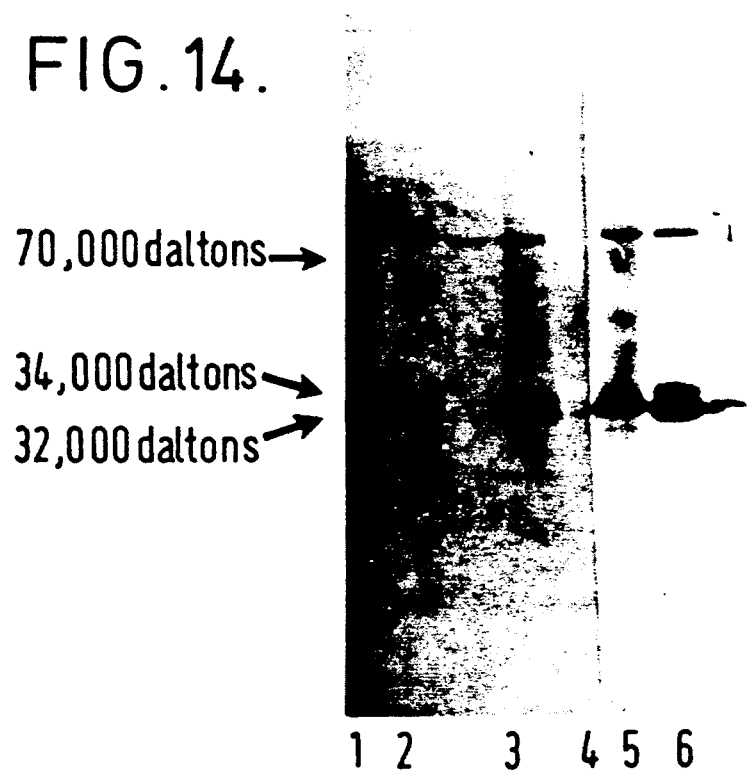

FIG. 14: Immunoblots. Immunoblots were obtained by the procedure described in Example 5. Lane 1: bovine aorta protein fraction with VAC-activity; Lane 2: bovine aorta protein fraction with VAC-activity; Lane 3: bovine lung protein fraction with VAC-activity; Lane 4: human umbilical cord artery protein fraction with VAC-activity; Lane 5: rat aorta protein fraction with VAC-activity; and Lane 6: horse aorta protein fraction with VAC-activity.

Figure 15:
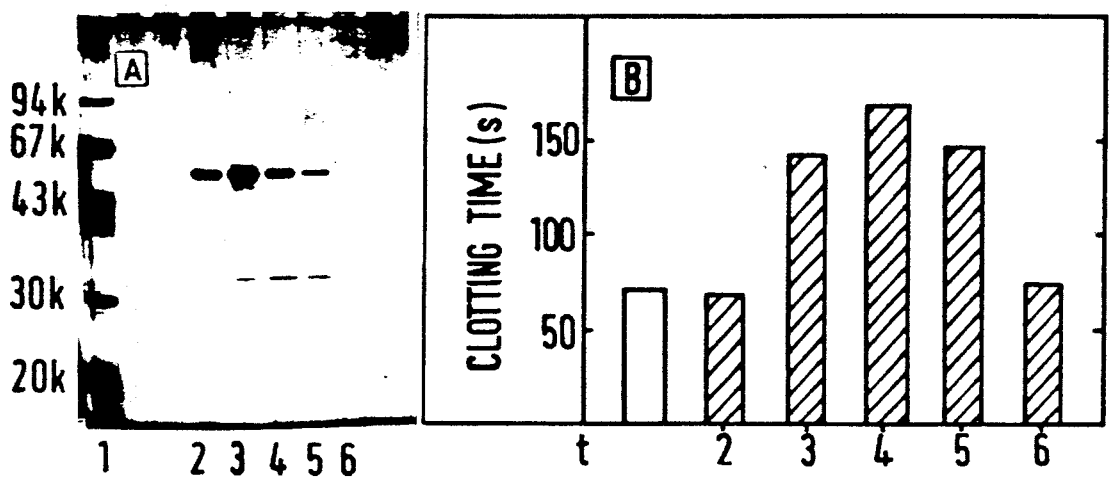

FIG. 15: Gel Electrophoresis (A) and Anti-Coagulant Activity (B) of the Various Fractions of the G-75 Eluate. Various fractions of the G-75 eluate were subjected to gel electrophoresis as described. The bands were stained with silver by the method of Merril et al.,

*Electrophoresis J.*, 3: 17–23 (1982). Electrophoresis lane 1: low molecular weight standards; electrophoresis lanes 2–6: equal volumes of non-reduced G-75 fractions with increasing elution volume. Specific quantities of the G-75 fractions, which had been analyzed by gel electrophoresis, were tested in the MPTT using HTP to initiate coagulation. The control coagulation time is represented by the open bar. The figures under the shaded bars correspond to the numbers of the electrophoresis lanes in FIG. 15A.

Figure 16:
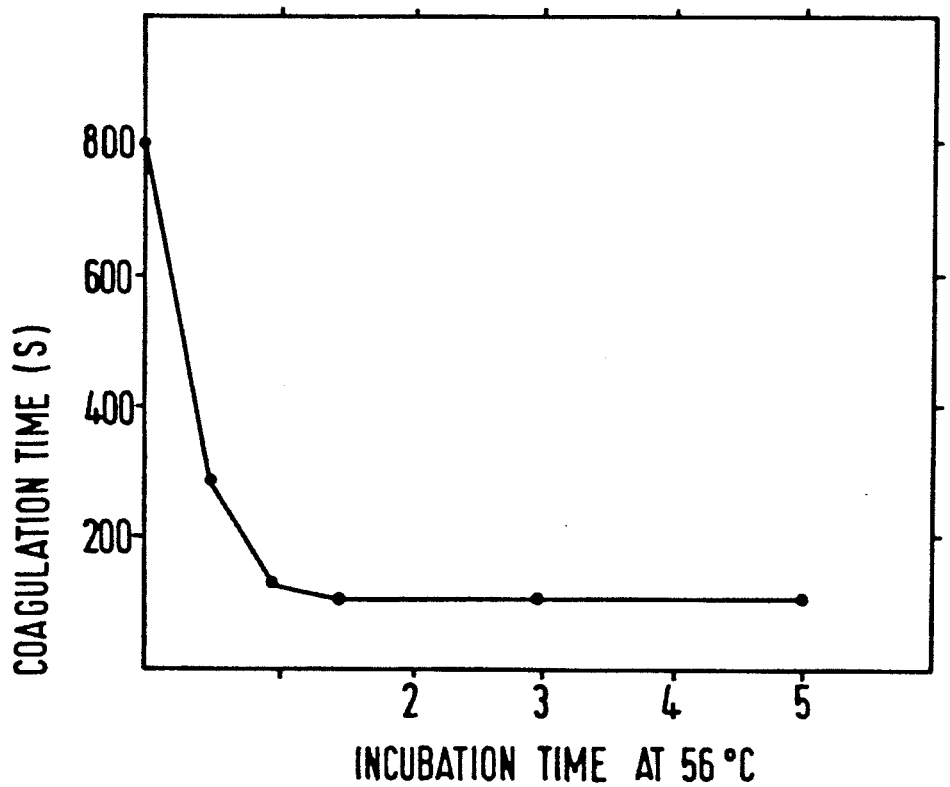

FIG. 16: Heat Inactivation of the Vascular AntiCoagulation Agent (VAC). The anti-coagulation agent was incubated at 56° C. and, after the various incubation periods, 5 μl samples containing 3.6 μg protein were taken, immediately cooled with ice, and tested in the MPTT using HPT as coagulation initiator The coagulation time of the control sample was 110 seconds

DESCRIPTION OF THE PREFERRED EMBODIMENTS

The present invention relates to an agent which has blood coagulation-inhibiting properties but not the disadvantageous side effects on the coagulation process which accompany the anti-coagulants currently known.

The anti-coagulant proteins of the invention do not deactivate the coagulation factors, but inhibit:
the modified prothrombin-time experiment and/or
the modified activated partial thromoplastin-time experiment and/or
the non-modified prothrombin-time experiment and/or
the prothrombin activation by the coagulation factor $X_a$ in the presence of negatively charged phospholipids and $Ca^{2+}$ and/or
the intrinsic X-activation by factor $IX_a$ in the presence of negatively charged phospholipids and $Ca^{2+}$ and/or
the prothrombin activation of isolated stimulated blood platelets and/or
the coagulation induced by the walls of the blood vessels and/or
the coagulation-dependent platelet aggregation.

The invention also relates to anti-coagulant proteins that do not inactivate the coagulation factors and whose inhibitory activity depends on the concentration of phospholipids. The proteins of the invention induce inhibition of prothrombin activation by factor $X_a$. This inhibition depends on the phospholipid concentration and is less at high phospholipid concentrations. Phospholipids are not hydrolyzed by the proteins of the invention.

The invention further relates to anti-coagulant proteins which do not inactivate the coagulation factors and which bind, via the divalent cations $Ca^{2+}$ and/or $Mn^{2+}$, to negatively charged phospholipids, which can be found, for example, in vesicles, liposomes or etherosomes and/or, via the divalent cations $Ca^{2+}$ and/or $Mn^{2+}$, to negatively charged phospholipids which are coupled with Spherocil. The binding of the anticoagulant proteins of the invention to negatively charged phospholipids is reversible and can be reversed by ethylenediamine tetraacetic acid (EDTA). The proteins according to the invention are capable of displacing factor $X_a$ and prothrombin from a negatively charged phospholipid surface.

The invention relates particularly to anti-coagulant proteins which do not inactivate the coagulation factors and have molecular weights of approximately $70 \times 10^3$, $60 \times 10^3$, $34 \times 10^3$, or $32 \times 10^3$, of which the proteins with a molecular weight of $34 \times 10^3$ or $32 \times 10^3$ have a single polypeptide chain.

The invention preferably relates to a family of anti-coagulant proteins which do not inactivate the coagulation factors and are characterized in that:
they are isolated from the walls of blood vessels in mammals and are then substantially purified,
they are not glycoproteins,
they are not phospholipases,
they have an isoelectric point of pH 4.4–4.6,
the activity of the anti-coagulant proteins at 56° C. is thermally unstable,
the activity of the anti-coagulating proteins in citrated plasma remains stable for some hours at 37° C.,
the activity of the anti-coagulant proteins is not completely destroyed by trypsin and/or chymotrypsin,
the activity of the anti-coagulant proteins is not affected by collagenase and/or elastase,
they bind, via the divalent cations $Ca^{2+}$ and $Mn^{2+}$, to negatively charged phospholipids which can be found in vesicles, liposomes or etherosomes,
they bind via the divalent cations $Ca^{2+}$ and $Mn^{2+}$ to negatively charged phospholipids which are coupled to Spherocil,
the binding of the proteins to the negatively charged phospholipids is reversible and can be removed by ethylenediamine tetracetic acid (EDTA),
they displace factor $X_a$ and prothrombin from a negatively charged phospholipid surface,
they inhibit the modified prothrombin-time experiment,
they inhibit the modified, activated, partial thromboplastin-time experiment,
they inhibit the non-modified prothrombin-time experiment,
they inhibit prothrombin activation by the coagulation factor $X_a$ in the presence of negatively charged phospholipids and $Ca^{2+}$ in vitro,
they do not inhibit the biological and amidolytic activity of factors $X_a$ and $II_a$,
they inhibit the intrinsic X-activation by the factor $IX_a$ in the presence of negatively charged phospholipids and $Ca^{2+}$ in vitro,
they inhibit the prothrombin activation of isolated stimulated blood platelets in vitro,
they inhibit the coagulation induced by the walls of the blood vessels in vitro, and
the inhibition of prothrombin activation by factor $X_a$ induced by the proteins is dependent on the concentration of phospholipids and is reduced at high phospholipid concentrations.

In particular, the invention relates to VAC proteins substantially free of any animal tissue, especially in substantially pure form.

Suitable starting materials for the isolation of the VAC proteins are the blood vessel walls and highly vascularized tissue of various mammals, for example, cattle, rats, horses, and humans, as well as endothelial cell cultures of these mammals. The arterial walls of cattle, rats, horses, and humans and human umbilical veins and arteries are particularly suitable.

The invention also relates to a process for preparing the proteins of the invention using isolation and purification techniques. In a procedure which is particularly suitable, the starting material is homogenized and subjected to differential centrifugation. The supernatant liquid obtained can then be further treated as follows in any desired sequence. Undesirable contaminants can be precipitated with ammonium sulfate. The supernatant is then further purified by affinity chromatography, for example, using hydroxyapatite; ion exchange chromatography, for example, using DEAE-Sephacel; chromatography over a molecular sieve, such as Sephadex G-100, and immunoabsorption chromatography, for example, with polyclonal or monoclonal antibodies. Depending on the quality of the starting material the purification process can be modified or other purification procedures can be used such as, for example, phospholipid vesicles.

In addition to the classic anti-thrombosis treatment, namely, coagulants taken orally, more recently biosynthetic tissue-plasminogen activator has been administered by the intrasvascular route for cases of manifest thrombosis (*N. Engl. J. Med.*, 310: 609-513 (1984)).

The proteins according to the present invention are especially suitable for preventing thrombosis, for example, during operations, because of their blood coagulation-inhibiting properties while at the same time inhibiting the coagulation-dependent aggregation of platelets.

The present invention therefore also relates to the use of the proteins according to the invention as antithrombotic agents.

The invention further relates to pharmaceutical compositions which comprise at least one protein according to the invention in association with a pharmaceutically acceptable carrier and/or excipient.

The anti-coagulant proteins of the invention can be administered parenterally by injection or by gradual perfusion over time. They can be administered intravenously, intraperitoneally, intramuscularly, or subcutaneously.

Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers, such as those based on Ringer's dextrose, and the like. Preservatives and other additives can also be present, such as, for example, antimicrobials, antioxidants, chelating agents, inert gases, and the like. See, generally, *Remington's Pharmaceutical Science*, 16th Ed., Mack, eds. 1980.

The invention also relates to a method for preparing a medicament or pharmaceutical composition comprising the components of the invention, the medicament being used for anti-coagulant therapy.

Figure 1:
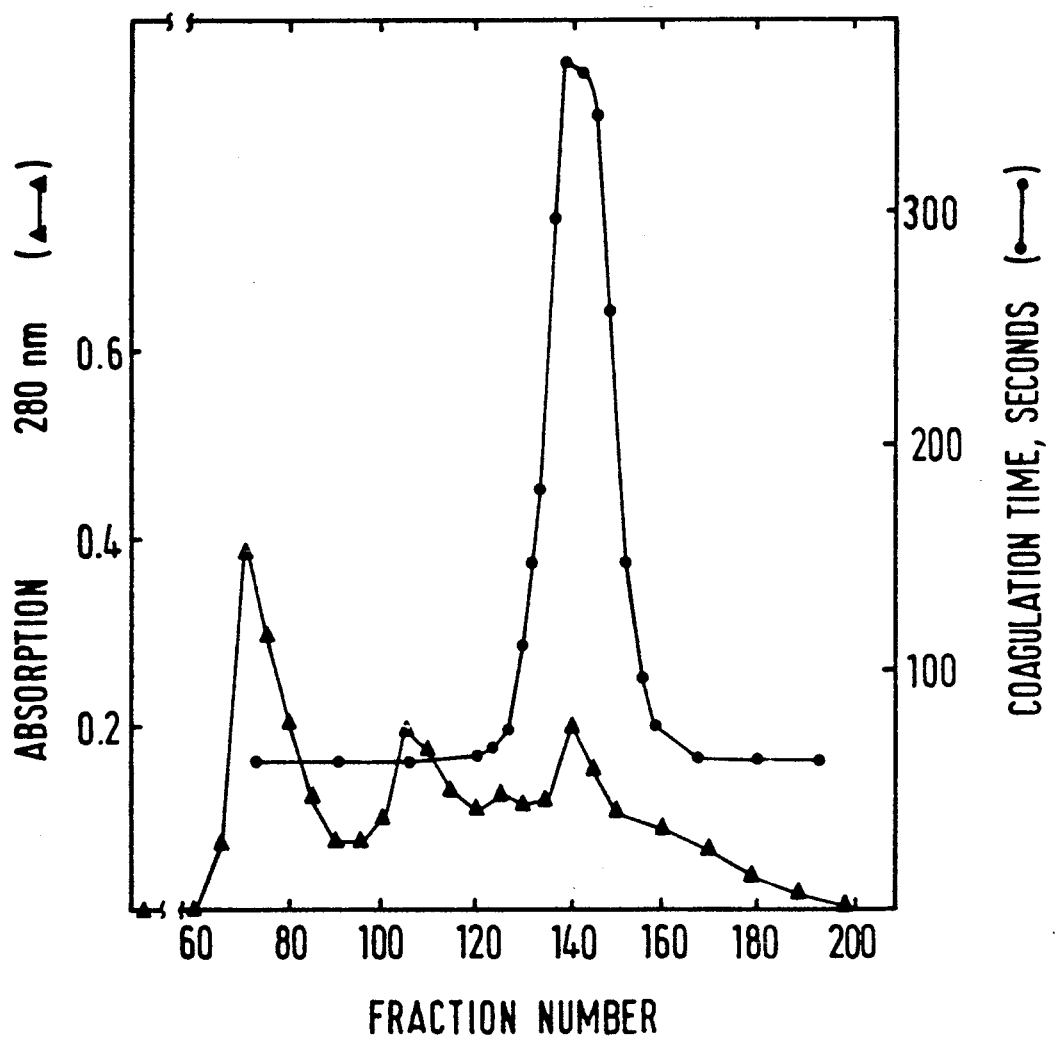
FIG. 1: Gel Filtration of VAC on Sephadex G-100. The column (3×80 cm) was prepared at 60 cm pressure and equilibrated with 500 mM NaCl and 20 mM Tris/HCl, pH 7.5. The VAC-containing fraction obtained after DEAE chromatography was concentrated (2 ml) and then passed over the Sephadex G-100. The pressure was maintained at 60 cm. and the void volume was 245 ml (fraction 70). The fractions (2 ml) were dialyzed against Tris-buffered saline (TBS) containing 10% glycerol, and tested for VAC activity by the one-stage coagulation test as described in Example 1. The coagulation times were determined using 1:10 dilutions of the G-100 fractions in TBS. The coagulation time in the absence of VAC was 65 seconds.

Results from the isolation and purification of VAC from bovine arteries are shown in Table A. Determination of the level of VAC activity in the supernatant of the 100,000×g centrifugation was erroneous owing to the presence of procoagulant activity. The components responsible for this activity were found to be precipitated with ammonium sulfate at a saturation level of 35%. It was discovered that the supernatant solution obtained after precipitation with 35% ammonium sulfate contained 100% VAC activity. In order to precipitate this activity, the solution was mixed with ammonium sulfate until 90% saturation was achieved. The resulting precipitate containing the VAC proteins was bound to a hydroxyapatite column in the presence of TBS (100 mM NaCl, 50 mM Tris/HCl, pH 7.5). After washing, the VAC proteins were eluted from this column with an increasing phosphate gradient. At low ion concentration, the VAC proteins were bound to the DEAE-Sephacel column. Elution of the VAC proteins from this column was done using an increasing NaCl concentration gradient. In the final purification step, the proteins were separated on the basis of their molecular weight by gel filtration on Sephadex G-100. A high-salt buffer was used as the eluant to minimize the interaction of VAC with the Sephadex material. VAC was eluted from this column in a volume of about 1.6 times the void volume of the column (see FIG. 1). The total yield of VAC after this final purification was 35%. By SDS-PAGE, all G-100 fractions which showed VAC activity were found to contain two polypeptides (molecular weight 34,000 and 32,000, respectively). In some cases, an additional fraction with a molecular weight of 60,000 showed VAC-activity.

Using SDS-PAGE, only peak fractions 138-140 were homogeneous in relation to the two polypeptides. These fractions were used for all other experiments concerning investigation of bovine VAC described in the specification, with the exception of the experiments for characterizing the binding of bovine VAC to phospholipid liposomes.

In G-100 fraction 139, 3.4% of the VAC activity was found to have a specific activity of 1480 units per mg of protein by means of a one-stage coagulation test (see Example 1 and Table A). This fraction contained no detectable quantity of phospholipid. An extinction coefficient of $$A^{1\%}_{1\,cm} = 8.5$$

was calculated for this purified VAC preparation from the absorption at 280 nm and from the protein content.

Figure 2:
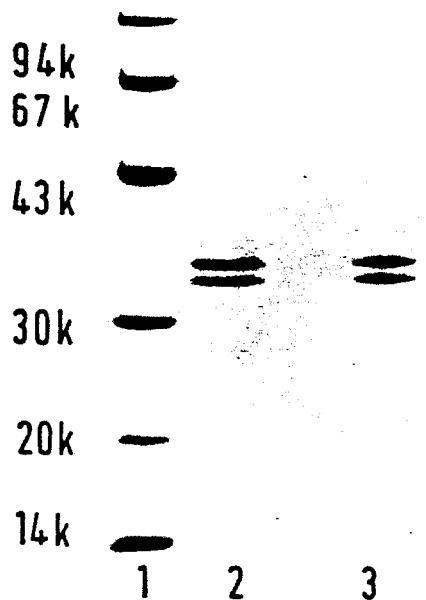
FIG. 2: Analytical SDS-PAGE of VAC. SDS-PAGE gels contained by weight 10% acrylamide, 0.27% of N,N$^3$-methylene-bisacrylamide, and 0.1% SDS (Laemli, U K., *Nature,* 227: 680-685 (1970)):
Lane 1: reduced reference proteins;
Lane 2: 25 µg reduced VAC;
Lane 3: 25 µg non-reduced VAC.
The gel was stained with Coomassie Blue and decolorized in the manner described in Example 1.
Figure 3:
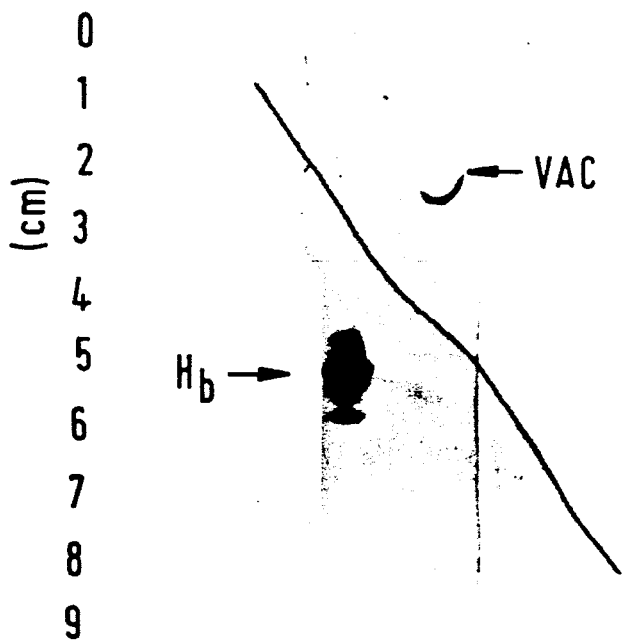
FIG. 3: Isoelectric pH of VAC. Electrofocusing was carried out with PAG plates in a pH range of from 3.5-9.5 (see Example 1). 200 µg of human H$_b$[1] and 20 ug of VAC were applied to the gel after the pH gradient had formed in the gel. Human H$_b$ was used as a reference (isoelectric point: pH 6.8). The gel was fixed for 30 minutes with 0.7M trichloroacetic acid and stained with Coomassie Blue.

As shown in FIG. 2, the two polypeptides with molecular weights of 34,000 and 32,000, which are present in the purified protein material from bovine arteries and to which VAC activity has been ascribed, have a single polypeptide chain. Using Schiff's reagent with basic fuchsin, it was established that both proteins contain few carbohydrate groups. Moreover, no gamma-carboxyglutamate (Gla) residues could be found in either protein. Isoelectric focusing (Example 1) showed that both proteins migrate in a single band corresponding to an isoelectric point of 4.4 to 4.6 (FIG. 3).

The VAC activity was obtained from the PAG plate by elution of this band from the gel. Analysis of the eluant with SDS-PAGE again showed the presence of the two proteins. It was thus possible to confirm that both proteins migrate in a single band in the pH gradient of the PAG plate. In order to check the method, human hemoglobin (Hb) was also investigated by isoelectric focusing. The value of 6.8 found for Hb agrees with the value given in the literature (see FIG. 3).

Binding experiments showed that the VAC activity can bind to negatively charged phospholipid membranes. This binding takes place in the presence of $Ca^{2+}$ and $Mn^{2+}$, but not in the presence of $Mg^{2+}$ or in the absence of divalent metal ions (see Table B). This binding of VAC activity to liposomes is reversible using EDTA.

Figure 4:
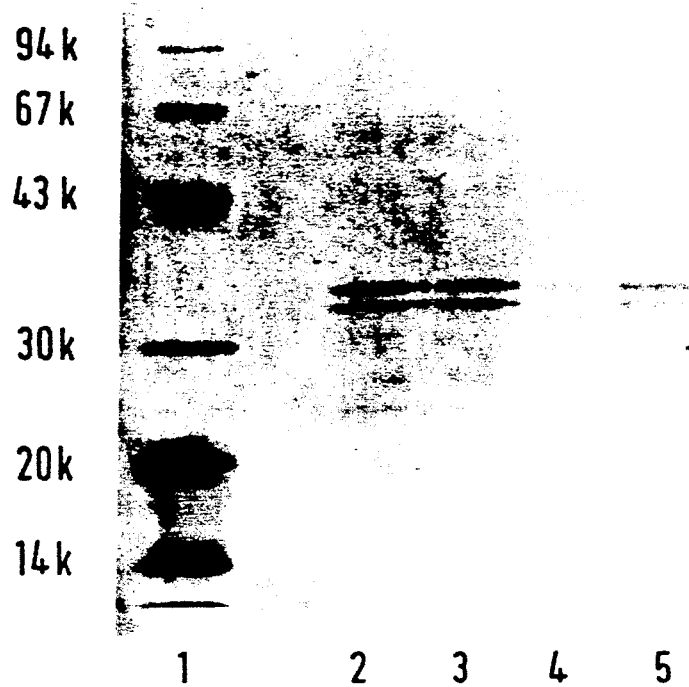
FIG. 4: Analysis of the Binding of VAC to Negatively Charged Phospholipid Liposomes with SDS-PAGE. SDS-PAGE was carried out according to Laemli (Laemli, U. K., *Nature,* 227: 680–685 (1970)) on the same plates as described in Example 1. The samples analyzed were obtained from the binding experiments as mentioned in the explanation to Table B.

Using SDS-PAGE, it was possible to show that both proteins can bind to liposomes in the presence of $Ca^{2+}$ and that this binding is disrupted when EDTA is added (see FIG. 4). This is yet another indication that VAC activity can be ascribed to these two proteins.

On storage in tris-buffered saline (TBS) containing 10% glycerol, VAC activity is stable at $-70°$ C. for at least three months, at $0°$ C. for at least 12 hours, and at $37°$ C. for at least half an hour. At $56°$ C., the activity disappears within two minutes.

The activity of VAC prolongs the coagulation time in a one-stage coagulation experiment (Example 1) in which coagulation is triggered with thromboplastin from bovine brains (BTP). Replacement of BTP in this experiment with purified bovine thrombin or purified bovine factor $X_a$ showed that VAC prolongs the coagulation time only if factor $X_a$ is used to initiate coagulation; coagulation induced by thrombin is not affected by VAC. This indicates that VAC directly inhibits the factor $X_a$ activity or that there is some interaction with the prothrombinase complex.

In further testing, an amidolytic thrombin formation test using purified bovine factor $X_a$ and prothrombin was carried out. FIG. 5 shows that when prothrombin is activated in the presence of $Ca^{2+}$ and phospholipid by means of factor $X_a$ to form thrombin, VAC inhibits the prothrombin activation and the degree of inhibition is dependent on the concentration of VAC. Moreover, the inhibiting effect of VAC is greater at a lower concentration of phospholipid.

FIG. 6 shows the phospholipid dependency of the VAC-induced inhibition of prothrombin activation. It is significant that at a phospholipid concentration of zero the prothrombin activation by factor $X_a$ is not inhibited by VAC. Control tests showed that VAC itself has no affect on the system of measurement.

Incubation of 5 $\mu$M phospholipid [1,2-dioleoylsn-glycero-3-phosphoserine (PS)/1,2-dioleoyl-sn-glycerol-3-phosphocholine (PC), 1:4 mol/mol] with 107 $\mu$g/ml VAC (specific activity: 1,300 units per mg) and 10 mM $Ca^{2+}$ reduced the procoagulant activity within 3 minutes at $37°$ C. This shows that VAC has no phospholipase activity.

In contrast to antithrombin 111 (AT-III), VAC has no effect on the amidolytic activity of purified thrombin and no lasting effect on factor $X_a$ activity, as measured with the chromogenic substrate S 2337 (N-benzoyl-L-isoleucyl-L-glutamyl-L-pipecolyl-glycyl-L-arginine-p-nitroanilide-dihydrochloride) or S 2238 (H-D-phenylalanyl-L-pipecolyl-L-arginine-p-nitroanilide-dihydrochloride) [see Table C]. This table also shows that the inactivation of factor $X_a$ and thrombin by AT-III is not intensified by VAC. Heparin, on the other hand, decisively increases inactivation of thrombin and factor $X_a$ in the presence of AT-III. This shows that VAC has neither a heparin-like activity nor an AT-III-like activity.

The isolation of the anti-coagulant of the invention from human tissue may be achieved by the same isolation procedure using, for example, a homogenate of human umbilical cord arteries. In such an homogenate, an anti-coagulant according to the present invention has been discovered by its ability to prolong the clotting time in a prothrombin time test. The anti-coagulation activity became measurable after Sephadex G-100 fractionation of the arterial homogenate [See Example 4]. From further isolation procedures, this activity is associated with a water-soluble substance(s), that carries an overall negative charge at pH 7.9.

Analysis of Sephadex G-75 fractions with gel electrophoresis has shown a positive correlation between the intensity of the 32,000 MW band and the prolongation of the clotting time as measured with a modified prothrombin time test (MPTT) [See Example 4]. The connection between the 32K-band and anti-coagulant activity is demonstrated by the fact that only the 32K-band of the polyacrylamide gel has anti-coagulant activity. In combination with the findings that the anti-coagulant rapidly loses its activity when incubated at $56°$ C., and that proteolytic enzymes can destroy its activity, it is likely that the anticoagulant activity is expressed by a single protein with a molecular weight of 32,000 daltons.

Trypsin, in contrast to protease type I, is a poor inactivator of the anti-coagulant. This suggests that the anti-coagulant possesses only a small number of lysine- and arginine-residues that are accessible to trypsin. The nature of the anti-coagulant activity has been studied by initiating coagulation in different ways. Clotting, induced by either the vascular procoagulant, HTP (human brain thromboplastin), or factor $X_a$, is inhibited by the anti-coagulant; thrombin-induced clotting, on the other hand, is not. From these findings, one can conclude that the anti-coagulant interferes with thrombin formation, not with thrombin action.

Prothrombinase reconstituted from purified factors and prothrombin were used to further study the anticoagulant mechanism [See Example 4]. Under these experimental conditions, the anti-coagulant can inhibit the activation of prothrombin by complete prothrombinase (factor $X_a$, factor $V_a$, phospholipid, $Ca^{2+}$) and by phospholipid-bound factor $X_a$ (factor $X_a$, phospholipid, $Ca^{2+}$) but not by free factor $X_a$ (factor $X_a$, $Ca^{2+}$).

The time course for prothrombin activation in the presence of the anti-coagulant indicate an instantaneous inhibition of prothrombin activation which remains constant in time. This shows that the anticoagulant acts neither by a phospholipase, nor by a proteolytic activity. The fact that the activation of prothrombin by factor $X_a$ and $Ca^{2+}$ is not affected by the anti-coagulant at all, strongly indicates that the anti-coagulant mechanism of the vascular compound differs from that of the well known plasma protease inhibitors such as antithrombin III. Since Walker et al., Biochim. Biophys. Acta, 571: 333–342 (1979), have demonstrated that activated protein C does not inhibit prothrombin activation by factor $X_a$, $Ca^{2+}$ and phospholipid, it can also be concluded that this compound is not protein C and does not belong in Group 2 described above.

Preliminary binding studies indicate that the vascular anti-coagulant probably interferes with the lipid binding of factor $X_a$ and/or prothrombin. Whether the ability of the anti-coagulant to inhibit prothrombin activation completely accounts for its prolongation of the prothrombin time remains to be established.

The fact that this inhibitor can be found in various types of arteries, but not in poorly vascularized tissue indicates that a physiological modulator of hemostasis and thrombosis, active at the vascular level, has been found.

On the absis of the properties and activities of VAC which have been observed, the blood coagulation mechanism under the influence of VAC may be interpreted.

VAC binds via Ca²⁺ ions to negatively charged phospholipids which occur as a result of damage to the tissues and/or because of the stimulation of blood platelets, and thereby reduces the binding of specific coagulation factors (vitamin K-dependent coagulation factors) to the negatively charged phospholipid surface which acts as a catalytic surface for these coagulation factors (*Biochem. Biophys. Acta,* 515:163–205 (1985)). As a result, the phospholipid-dependent blood coagulation reactions are inhibited by VAC. On the basis of its mechanism of activity, VAC can be categorized in Group 3 described above.

However, a critical difference between VAC and the other known proteins of this group is that VAC does not hydrolyze phospholipids and therefore does not decompose any essential membrane structures.

Among the properties of VAC which have not hitherto been described for any of the known anti-coagulants is the fact that the anti-coagulation effect of VAC is dependent on the concentration of phospholipids in the coagulation process. This dependency means that the coagulation process which has been initiated, for example, by slight damage to the wall of the blood vessel and/or by slight activation of blood platelets, that is, by a thrombotic process, can be inhibited by VAC. On the other hand, the coagulation process which is triggered by severe damage to walls of blood vessels, wherein phospholipids are present in high concentrations, is not inhibited by VAC, because of high phospholipid concentrations. The danger of severe bleeding when using VAC is therefore extremely small. This property of VAC is in contrast to all the previously known anti-coagulants which render one or more of the coagulating factors ineffective and thereby increase the risk of severe bleeding.

Another surprising property of VAC is that it does not deactivate the coagulating factors themselves. Consequently, the coagulating factors can still perform their other functions. For example, some active coagulating factors also play a non-hemostatic role in the chemotaxis of the inflammatory cells which participate in the repair of damaged blood vessel walls.

This invention further describes a novel class of anti-coagulant proteins which do not inactivate the coagulation factors. The Examples serving to illustrate the invention and the properties listed should not restrict the invention in any way. Anyone skilled in the art will be able, without any inventive effort, to obtain other proteins which have anti-coagulant properties without inactivating the coagulation factors, using the method described. These proteins also fall within the scope of protection of this invention.

The abbreviations used in the invention have the following meanings:

VAC: vascular anti-coagulant
PFP: platelet free plasma
TBS: 100 mM NaCl, 50 mM Tris/HCl, pH 7.5
EDTA: ethylenediamine tetraacetic acid
TBSE: TBS with 2 mM of EDTA
BTP: thromboplastin from bovine brains
HTP: thromboplastin from human brains
TBSA: TBS with 0.5 mg/ml of human serum albumin, pH 7.9
S 2337: N-benzoyl-L-isoleucyl-L-glutamyl-L-pipecolyl-glycyl-L-arginine-p-nitroanilide-dihydrochloride
S 2238: H-D-phenylalanyl-L-pipecolyl-L-arginine-p-nitroanilide-dihydrochloride
AT-III: human antithrombin III
S.A.: specific activity
Ole₂Gro-P-Cho: 1,2,-dioleolyl-sn-glycero-3-phosphocholine
Ole₂Gro-P-Ser: 1,2,-dioleolyl-sn-glycero-3-phosphoserine The nomenclature of the blood coagulation factors used was that recommended by the Task Force on Nomenclature of Blood Clotting Zymogens and Zymogen Intermediates.

Having now generally described this invention, the same will be better understood by reference to certain specific examples which are included herein for purposes of illustration only and are not intended to be limiting of the invention unless otherwise specified. Particularly, it is noted that, in principle, the present invention applies to all anti-coagulants from human and other animal sources, provided that they satisfy the purity and reactivity criteria, and also to preparations of the above-described compounds obtained by methods other than those disclosed herein.

EXAMPLE 1

Characterization of VAC a) Isolation and Purification of VAC

The chemicals for analytical SDS-PAGE and hydroxyapatite (HTP) were obtained from Bio-Rad. Sephadex G-100 and G-75, DEAE-Sephacel and the "Low Molecular Weight Calibration Kit" were obtained from Pharmacia. The chromogenic substrates S 2337 and S 2238 were obtained from Kabi Vitrum and the Diaflo PM-10 ultrafiltration membrane was obtained from Amicon.

Bovine aortas were taken within half an hour after slaughtering the animals. Bovine blood was collected in trisodium citrate (final concentration 0.38% by weight) and centrifuged for 10 minutes at ambient temperature at $2,000 \times g$. The plasma containing few blood platelets was then centrifuged again (15 minutes at $10,000 \times g$). In this way, platelet-free plasma was obtained (PFP).

The aortas from the animals were thoroughly rinsed with TBS (100 mM NaCl, 50 mM Tris/HCl, pH 7.5) immediately after being removed. The inner lining of the aortas was removed and homogenized using a high-speed homogenizer, e.g., the Braun MX 32, in TBSE (TBS with 2 mM EDTA) containing soyabean trypsin inhibitor (16 mg/l) and benzamidine (1.57 g/l).

The material homogenized from eight aortas and containing 20% solids (weight/volume) was centrifuged for 60 minutes at $100,000 \times g$. The supernatant was saturated with solid ammonium sulfate to 30% saturation, stirred from 30 minutes, and then centrifuged for 20 minutes at $12,000 \times g$. The resulting supernatant was saturated with solid ammonium sulfate to 90% saturation, stirred for 30 minutes, and centrifuged for 20 minutes at $12,000 \times g$.

The precipitate was suspended in a small volume of TBS and dialyzed with TBS containing benzamidine (1.57 g/l). The dialyzed fraction was applied to a hydroxyapatite column ($1 \times 20$ cm) which had been equilibrated with TBS. The column was washed with four bed volumes of TBS and the VAC proteins eluted with 200 ml of sodium phosphate buffer (pH 7.5) using a linear gradient (0–500 mM). The fractions containing VAC were combined and dialyzed against 50 mM of NaCl with 20 mM of Tris/HCl at pH 7.5.

This same buffer was used to equilibrate a DEAESephacel column ($3 \times 5$ cm) on which the dialyzed VAC material was chromatographed. The column was washed with four bed volumes of the equilibration buffer and the VAC eluted with 200 ml of NaCl solution in 20 mM of Tris/HCl, pH 7.5, using a linear gradient (50–300 mM). The fractions containing VAC were collected, dialyzed with 500 mM NaCl in 20 mM of Tris/HCl at pH 7.5 and then concentrated in an Amicon concentration cell using a PM-10 ultrafiltration membrane. The concentrate (2 ml) was applied to a Sephadex G-100 column (3×80 cm) equilibrated with 500 mM NaCl in 20 mM Tris/HCl, pH 7.5.

The eluate was collected in 2 ml fractions and the active fractions dialyzed separately against TBS containing 10% by volume glycerol and stored at −70° C. The entire purification was carried out at 0°–4° C.

b. Determining VAC Activity

Two different methods (see, generally, Harrison's *Principles of Internal Medicine*, 10th Ed., Petersdorf et al., eds., 1983) were used to determine the VAC activity:

(a) the one-stage coagulation test (modified prothrombin time test)
(b) thrombin formation test.

The one-stage coagulation test was carried out as follows:

In a siliconized glass dish, 175 μl of the fraction to be tested, or 175 μl of TBS as control, were stirred with 50 μl of PFP and 25 μl of dilute BTP (900 rpm). After incubation (3 minutes at 37° C.), coagulation was initiated by adding 250 μl of buffer which contained 80 mM NaCl, 20 mM CaCl$_2$, and 10 mM Tris/HCl, pH 7.5. Fibrin formation was recorded optically using a "Payton Dual Aggregation Module" (Hornstra, G., *Phil. Trans. R. Soc. London B*, 294: 355-371 (1981)). The coagulation time of the control sample was 65 seconds. This test was used during purification to examine the various fractions for the presence of VAC activity. In order to determine the VAC yield during purification, one unit of VAC activity was defined as the quantity of VAC which prolongs the coagulation time in the above test to 100 seconds.

In some cases, BTP was replaced by purified bovine thrombin or the purified bovine factor X$_a$. In this semi-purified coagulation system, the quantity of thrombin or factor X$_a$ used were such that the coagulation time of the control sample was also 65 seconds.

The thrombin formation test was carried out as follows:

20 μl of purified bovine factor X$_a$ (150 nM), 30 μl of CaCl$_2$ (100 mM), 30 μl of dilute VAC and 30 μl of PS/PC-phospholipid membrane (the final concentrations are given in the legend accompanying FIG. 6) were placed in a plastic dish containing 181 μl TBSA (TBS with 0.5 mg/ml human serum albumin, pH 7.9).

This mixture was stirred for 3 minutes at 37° C. with a Teflon stirrer. Thrombin formation was initiated by adding 9 μl of purified bovine factor 11 (33.33 uM). At various times, 50 μl samples of the reaction mixture were added to a plastic dish containing 900 μl of TBSE and 50 μl of chromogenic substrate S 2238 (5 mM, 37° C.). The concentration of thrombin in the reaction mixture was calculated from the change in extinction at 405 nm (Kontron Spectrometer Uvikon 810), using a calibration curve plotted from assays with known quantities of purified bovine thrombin. The percent inhibition caused by VAC was defined as follows:

$$\% \text{ inhibition} = \left(1 - \frac{a}{b}\right) \times 100\%,$$

wherein "a" is the rate of thrombin formation in the absence of VAC in nM II$_a$/min, and "b" is the rate of thrombin formation in the absence of VAC in nM II$_a$/min.

The vitamin K-dependent factors prothrombin and factor X$_a$ were obtained by purification of citrated bovine plasma (cf. Stenflo, J., *J. Biol. Chem.*, 251:355-363 (1976)). After barium citrate absorption and elution, fractionation with ammonium sulfate, and chromatography on DEAE-Sephadex, there were two protein fractions which contained a mixture of prothrombin and factor IX or factor X. Factor X was activated using the method of Fujikawa et al., *Biochemistry*, 11: 4882-4891 (1972) and using RVV-X (Fujikawa et al., *Biochemistry*, 11: 4892-4899 (1972)). Prothrombin was separated from factor IX by heparinagarose affinity chromatography (Fujikawa et al., *Biochemistry*, 12: 4938-4945 (1973)). The prothrombin-containing fractions from the heparin-agarose column were combined and further purified using the method of Owens et al., *J. Biol. Chem.*, 249: 594-605 (1974). The concentrations of prothrombin and factor X$_a$ were determined using the method of Rosing et al., *J. Biol. Chem.*, 255: 274-283 (1980). BTP was prepared by the method of Van Dam-Mieres et al., *Blood Coagulation Enzymes, Methods of Enzymatic Analysis*, Verlag Chemie GmbH, Weinheim. The protein concentrations were determined according to Lowry et al., *J. Biol. Chem.*, 193: 265 (19511)

C. PREPARATION OF PHOSPHOLIPIDS, PHOSPHOLIPID MEMBRANES AND PHOSPHOLIPID LIPOSOMES

Phospholipids were prepared using 1,2-dioleoyl-sn-glycero-3-phosphocholine (18:1$_{cis}$/18:1$_{cis}$-PC) and 1,2-dioleoyl-sn-gycero-3-phosphoserine (18:1$_{cis}$/18:1cis-PS), as described by Rosing et al., *J. Biol. Chem.*, 255: 274-283 (1980). Separate phospholipid membranes of PC and PS consisting of two layers were prepared using ultrasound as described by Rosing et al., *J Biol. Chem.*, 255: 274-283 (1980). A supply of phospholipid liposomes was prepared by dissolving the appropriate amount of phospholipid in chloroform which was evaporated using nitrogen. The residual phospholipid was suspended in TBS containg 5% glycerol, carefully mixed with a few glass beads for 3 minutes, then centrifuged for 10 minutes at 10,000×g. The above solution was discarded and the residue carefully resuspended in TBS containing 5% glycerol. In this manner, the phospholipid-liposome supply solution was obtained. These liposomes were stored at ambient temperature. The phospholipid concentration was determined by phosphate analysis according to Bottcher et al., *Anal. Chim. Acta.*, 24: 203-207 (1961).

Gel electrophoresis on plates in the presence of SDS was carried out according to the method described by Laemmli, *Nature*, 227: 680-685 (1970) using a gel which contained 10% by weight acrylamide, 0.27% by weight N,N$^3$-methylene-bisacrylamide and 0.1% by weight SDS. In gel samples with reduced disulfide bridges, 5% by weight beta-mercapto-ethanol was present. The gels were stained as follows:

(1) 0.25% by weight Coomassie Blue R-250 in 50% by weight ethanol and 15% by weight acetic acid, and decolorized with 10% by weight ethanol and 10% by weight acetic acid, or (2) with Schiff's reagent prepared from basic fuchsin (Merck) by the method of Segrest et al., described in *Methods in Enzymology*, Vol. 28, 54–63 (1972), or (3) with silver as described by Merril et al. in *Electrophoresis*, 3:17–23 (1982).

The isoelectric pH measurements of proteins were done using thin layer polyacrylamide gels which contain ampholine carrier ampholyte (PAG plates, LKB) at a pH range of 3.5–9.5 in accordance with the manufacturer's instructions. The pH gradient in the gel was determined immediately after electrofocusing by cutting off a strip of the gel along a line between the anode and the cathode. The electrolytes were eluted from each strip using distilled water and the pH measured with a combined glass electrode.

The Gla determination was carried out by HPLC on a "Nucleosil 5SB" column (CHROMPACK) using the method of Kuwada et al., *Anal. Biochem.*, 131: 173–179 (1983).

EXAMPLE 2

Coupling of Phospholipids to Spherocil

The required phospholipids were dissolved in chloroform and added to the column material (Spherocil, Messrs. Rhone-Poulenc) at a ratio of 5 mg of phospholipid per gram of Spherocil. The chloroform was evaporated with $N_2$ gas and the dry Spherocil phospholipid was then washed with the buffer in which VAC had been suspended. VAC binds to Spherocil-coupled phospholipid in the presence of $Ca^{++}$ and/or $Mn^{++}$ when some of the phospholipids are negatively charged.

EXAMPLE 3

50 μl of citrated/platelet-free plasma were mixed with 200 μl of buffer (25 mM Tris/HCl, pH 7.5, 100 mM NaCl), containing kaolin (catalyzes coagulation), inositin (phospholipid source) and VAC were present. This mixture was incubated (3 minutes at 37° C.) and 250 μl of $Ca^{++}$ buffer (200 mM Tris/HCl, pH 7.5, 80 mM NaCl, 20 mM $CaCl_2$) was added. The coagulation time was measured as described in Example 1.

EXAMPLE 4

Isolation and Characterization of Anti-Coagulant From Human Tissue

Human blood was collected by venipuncture in trisodium citrate (13 mM) and centrifuged at 2,000×g for 10 minutes at room temperature. The resulting plasma was recentrifuged at 1,000×g for 15 minutes in order to obtain platelet free plasma (PFP). A standard pool of PFP was prepared by mixing plasma from several healthy donors.

Human umbilical cords were obtained within 15 minutes after delivery. The arteries were immediately perfused with ice-cold TBS-buffer, subsequently prepared free from the Jelly of Warton, and homogenized in TBS using a whirl mixer (Braun MX32). A 10% homogenate (w/v) was then fractionated.

Fractionation of the supernatant from a 10,000×g centrifugation of the homogenate on Sephadex G-100 results in a reproducible profile (see FIG. 7). The fractions affecting the coagulation system as measured with the MPTT are indicated in FIG. 7. Procoagulant activity eluted with the void volume. This activity can only be detected in the presence of factor VII in the MPTT, as indicated by experiments in which human congenital factor VII-deficient plasma was used. This establishes that this procoagulant is tissue thromboplastin.

Certain fractions showed a distinct anti-coagulant activity. These fractions were pooled and further purified with DEAE-Sephacel chromatography (see FIG. 8A). The anti-coagulant bound to the DEAE-Sephacel with 50 mM NaCl in 50 mM Tris/HCl, pH 7.9. Elution of activity with a linear gradient of NaCl at pH 7.9 was achieved at 150–160 mM NaCl. The DEAE-fractions expressing anti-coagulant activity were pooled and filtered using Sephadex G-75 (FIG. 8B). The column (1.5×50 cm) was equilibrated with TBS and activity was present in those fractions which corresponded to molecular weights of about 30,000–60,000 daltons.

The MPTT was used as a quantitative assay for the determination of the amount of anti-coagulant activity (see FIG. 9). One unit of anti-coagulant activity was defined as that quantity which prolongs the clotting time in the MPTT, with HTP (final concentration 95 μg protein/ml) as initiator of coagulation, from its control value of 65 s to 100 s. With this assay, it was calculated that from 10 g wet arterial tissue 2 mg protein with approximately 1,200 units anti-coagulant activity can be isolated.

The modified prothrombin time test (MPTT) was carried out as follows:

In a siliconized glass cuvette, 50 μl PFP was stirred at 37° C. with 150 μl TBS, 25 μl of a standard HTP-dilution, and 25 μl TBS (control) or 25 μl of a fraction of the arterial homogenate After incubation for 3 minutes, coagulation was started at time zero with the addition of 250 μl $Ca^{2+}$-buffer (80 mM NaCl, 20 mM $CaCl_2$ and 10 mM Tris/HCl, pH 7.9). Fibrin formation was monitored optically (Payton Dual Aggregation Module). When factor $X_a$ was utilized to initiate coagulation in the MPTT, HTP was omitted and 25 μl purified factor $X_a$ was added together with the 250 μl $Ca^{2+}$-buffer to the diluted PFP.

The modified thrombin time test (MTT) was carried out similar to the $X_a$-initiated MPTT described above, with the exception that the $X_a$-preparation was replaced by 25 μl of purified thrombin Protease type I and trypsin (EC 3.4.2.1.4) were obtained from Sigma. HTp was prepared from human brain as described by van Dam Mieras et al., *Methods of Enzymatic Analysis*, 5: 352–365 (1984). Factor $X_a$, prothrombin and thrombin were purified from citrated bovine blood as described by Rosing et al , *J. Biol. Chem.*, 255: 274–283 (1980). Factor V was purified from bovine blood as described by Lindhout et al., *Biochemistry*, 21 4594–5502 (1982). Factor $V_a$ was obtained by incubating factor V with thrombin. Prothrombin concentrations were calculated from MW=72,000 and $A_{280}^{1\%}$=9.6 (Owen et al., *J. Biol. Chem.* 249: 594–605 (1974), and factor V concentration was calculated from MW=330,000 and $A_{280}^{1\%}$=9.6 (Nesheim et al., *J. Biol. Chem.*, 254: 508–517 (1979). Factor $X_a$ and thrombin concentrations were determined by active site titration (Rosing et al., *J. Biol. Chem.*, 253:274–283 (1980). Other protein concentrations were determined as described by Lowry et al., *J. Biol. Chem.*, 193: 265 (1951).

Phospholipid and phospholipid vesicles were prepared using Ole₂Gro-P-Cho(1,2-dioleoyl-sn-glycero-3-phosphocholine) and Ole₂Gro-P-Ser(1,2-dioleoyl-sn-glycero-3-phosphoserine) as described in Rosing et al., supra (1980). Single bilayer vesicles composed of Ole$_2$-Gro-P-Ser/Ole$_2$Gro-P-Cho (molar ratio 20:80) were prepared by sonication. Phospholipid concentrations were determined by phosphate analysis according to the method of Bottcher et al., *Anal. Chim. Acta,* 24:203–207 (1961).

The time course of prothrombin activation was examined at different concentrations of anti-coagulant. Mixtures of ($X_a$, $Ca^{2+}$), ($X_a$, phospholipid, $Ca^{2+}$) or ($X_a$, $V_a$, phospholipid, $Ca^{2+}$) were stirred with different amounts of the anti-coagulant at 37° C. in 50 mM Tris/HCl, 175 mM NaCl, 0.5 mg/ml human serum albumin at pH 7.9. After 3 minutes, prothrombin activation was started by the addition of prothrombin. At different time intervals, a 25 μl sample was transferred from the reaction mixture into a cuvette (37° C.), containing TBS, 2 mM EDTA and 0.23 mM S 2238 (final volume: 1 ml). From the absorption change at 405 nm (Kontron Spectrophotometer Uvikon 810), and a calibration curve based on purified thrombin, the amount of thrombin formed was calculated at different concentrations of anti-coagulant.

Phospholipid was added in the form of vesicles composed of Ole$_2$Gro-P-Ser and Ole$_2$Gro-P-Cho with a molar ratio of 20:80.

Several fractions from G-75 chromatography were tested by MPTT and analyzed using SDS-PAGE. The results (FIG. 10) showed that the anti-coagulant has a molecular weight of approximately 32,000 daltons. The anti-coagulant activity of the 32K-band was confirmed by slicing the polyacrylamide gel, eluting the protein and testing the eluant for anti-coagulant activity as described above. Anti-coagulant activity was found only in the eluant in the slice corresponding to the 32K band. This activity was found to be stable at 56° C. and had a dose response relationship in the MPTT similar to the starting material.

The G-75 fractions containing the highest anticoagulant activity were pooled and used for further characterization of the anti-coagulant. Incubation of the anti-coagulant at 56° C. rapidly decreases its activity until after 2 minutes no activity can be measured. The anti-coagulant loses its activity completely within 2 hours upon incubation at 37° C. with protease type I, whereas trypsin has little effect on the anti-coagulant after an incubation period of 3 hours (FIG. 11). The protease type I and the trypsin concentration used in these experiments, completely inactivate 2.5 nM thrombin in 15 minutes. The amounts of protease type I and trypsin, carried over from the reaction mixtures to the MPTT, have no effect on the control clotting time.

The MPTT is prolonged in the presence of the anti-coagulant (FIG. 12) both when initiated with HTP and when started with factor $X_a$. Thrombin-induced coagulation, however, is not inhibited.

Because of these findings, we investigated the effect of the anti-coagulant on the conversion of prothrombin to thrombin by factor $X_a$, factor $V_a$, phospholipid and $Ca^{2+}$. Under the experimental conditions mentioned, thrombin formation is inhibited by the anti-coagulant in a dose-dependent way (FIG. 13A). The activation of prothrombin by factor $X_a$, phospholipid and $Ca^{2+}$ in the absence of factor $V_a$ can be inhibited also by the anti-coagulant (FIG. 13B). However, this inhibition is not observed if the activation takes place in the absence of phospholipid (FIG. 13C).

EXAMPLE 5

Polyclonal Antibodies Against VAC Polyclonal antibodies against bovine VAC were raised in a rabbit. Bovine VAC, purified according to the method as described in Example 1, was mixed with equal amounts of complete Freund's adjuvant. The mixture was injected subcutaneously into a rabbit. After a period of 4 weeks, the rabbit was re-injected subcutaneously with purified bovine VAC. The subcutaneous injections were repeated twice at two-week intervals. Ten days after the last injection, the rabbit was bled and the collected blood was allowed to clot in order to obtain serum.

Immunoglobulins (Ig) were isolated from the serum according to the following method:
(a) The serum was heated for 30 minutes at 56° C.
(b) Subsequently, the serum was applied to DEAESephacel, which was equilibrated with 50 mM Tris, 100 mM NaCl, pH 8.2.
(c) The non-bound protein was precipiptated with $(NH_4)_2SO_4$ at 50% saturation.
(d) The precipitated proteins were pelleted by centrifugation and the pellet resuspended in 50 mM Tris, 100 mM NaCl, pH 7.9 and dialyzed extensively against the same buffer.
(e) The resulting protein mixture contained anti-VAC Ig.

Following the procedure as described, protein fractions which express VAC-activity were isolated from bovine aorta, bovine lung, rat and horse aorta, and human umbilical cord arteries.

The proteins were separated by electrophoresis on a polyacrylamide gel in the presence of dodecyl sulfate and under non-reduced conditions. After completion of the electrophoresis, the proteins were transferred from the gel to nitrocellulose sheets as described by Towbin et al., *Proc. Natl. Acad. Sci., USA,* 76: 4350–4354 (1979). The sheets were incubate with the anti-VAC Ig and after thorough washing the sheets were incubated with goat anti-rabbit Ig coupled to horseradish peroxidase. The latter was visualized with the peroxidase substrate diamine bezidine tetrahydrochloride.

A brown band on the nitrocellulose sheet, after completion of the described procedure, indicated the presence of goat anti-rabbit Ig. Furthermore, on this spot were present anti-VAC Ig and proteins to which the anti-VAC Ig was bound.

Immunoblots of proteins with VAC activity, isolated from bovine aorta, bovine lung, rat and horse aorta, and human umbilical cord arteries are presented in FIG. 14.

These results show that by essentially using the isolation procedure as described, a protein fraction with VAC activity can be obtained from bovine aorta, bovine lung, rat and horse aorta, and human umbilical cord arteries. Moreover, the isolated protein fractions with VAC activity contain proteins, with MW of approximately 32,000, 34,000, and 70,000, that react with anti-VAC Ig raised against purified bovine VAC in rabbits.

EXAMPLE 6

Purification of VAC, Using Large Volume Phospholipid Vesicles

Large volume phospholipid vesicles (LVV), composed of 1,2-dioleoyl-sn-glycero-3-phosphoserine (PS) and 1,2-dioleoyl-sn-glycero-3-phosphocholine ), (PC), were prepared by the method of P. van de Waart et al., *Biochemistry*, 22: 2427–2432 (1983).

For the purification step, LVV containing PS/PC (molar ratio 20:80) was used. Other molar ratios can be used as long as negatively charged phospholipids are present. The chain length of the fatty acids in the phospholipids can also be varied.

LVV, ±1 mM phospholipids in 50 mM Tris/HCl, 100 mM NaCl, pH 7.9, were mixed with an equal volume of a protein fraction containing VAC activity. The proteins were in 50 mM Tris/NaCl, 10 mM $CaCl_2$, pH 7.9. The mixture was allowed to stand for 5 minutes at ambient temperature. Subsequently, the mixture was centrifuged for 30 minutes at 20,000×g. The pellet was resuspended in 50 mM Tris/HCl, 100 mM NaCl, 10 mM $CaCl_2$, pH 7.9, and recentrifuged. The resulting pellet was then resuspended in 50 mM Tris/HCl, 10 mM ethylenediamine tetraacetic acid (EDTA), pH 7.9, and recentrifuged. The resulting supernatant contained the VAC activity.

The above described procedure is an efficient purification step in the procedure to obtain purified VAC.

TABLE A
Summary of the Purification of VAC from Inner Coat of Bovine Aorta

| Purification Step | Protein[a] mg | VAC[b] Units | Specific Activities units/mg | Yield % | Degree of Purification |
|---|---|---|---|---|---|
| Supernatant liquid with 35% $(NH_4)_2SO_4$ | 630 | 19.000 | 31.0 | 100 | 1.0 |
| Precipitate with 90% $(NH_4)_2SO_4$ | 470 | 19.000 | 40.4 | 97 | 1.3 |
| Hydroxyapatite fraction | 206 | 17.300 | 84.0 | 89 | 2.7 |
| DEAE fraction | 35.8 | 13.900 | 388 | 71 | 12.5 |
| Sephadex G-100 fraction 139 | 0.45 | 0.666 | 1480 | 3.4 | 47.7 |

[a]Protein was determined using the method of Lowry et al. (J. Biol. Chem., 193: 265 (1951).
[b]The VAC units were determined using the one-stage coagulation test described in Example 1 by a series of test dilutions. The coagulation time of the control samples was 65 seconds. One unit of VAC activity was defined as the quantity of VAC which prolongs the coagulation time to 100 seconds.

TABLE B
Cation-Dependent Binding of VAC to Negatively Charged Phospholipid Liposomes

| Cation (10 mm) | $t_c$, seconds[a] Supernatant Liquid[b] | EDTA[c] |
|---|---|---|
| Control (no liposomes) | 180 | N.D.[d] |
| Control (no cation) | 174 | 64.8 |
| $CaCl_2$ | 64.2 | 134 |
| $MgCl_2$ | 165 | N.D. |
| $MnCl_2$ | 65.1 | N.D. |

[a]The coagulation time ($t_c$) was determined using the one-stage coagulation test described in Example 1.
[b]50 ul phospholipid liposomes (PS/PC; 50/50 mol/mp: 1 mm), 50 ul VAC (250 ug/ml, specific activity = 700 units per mg), and 100 ul of TBS containing 5% glycerol and cation, pH 7.5, were mixed at ambient temperature and centrifuged for 15 minutes at 15,000 xg. Supernatant liquid (25 ul) was diluted with TBS to a final volume of 175 ul and tested using the one-stage coagulation test. The remainder of the supernatant liquid was analyzed with SDS-PAGE (FIG. 4).
[c]The liposome precipitate was suspended in 150 ul of TBS containing 5% glycerol and 10 mm EDTA, pH 7.5. The suspension was centrifuged for 15 minutes at 15,000 xg. The VAC activity of the supernatant was analyzed as described above.
[d]N.D. = not determined.

TABLE C
Effect of VAC on the Amidolytic Activity of Factor $X_a$ and Factor $II_a$

| | VAC ($A_{405}$/min × $10^3$)[a] | |
|---|---|---|
| | − | + |
| $X_a$ | 110.5 | 110.5 |
| $X_a$, AT-III | 80.0 | 81.5 |
| $X_a$, Heparin | 110.5 | 109.0 |
| $X_a$, Heparin, AT-III | 47.5 | N.D.[b] |
| $II_a$ | 7.5 | 7.5 |
| $II_a$, AT-III | 5.4 | 5.6 |
| $II_a$, Heparin | 7.5 | 7.1 |
| $II_a$, Heparin, AT-III | 0.56 | N.D. |

[a]The amidolytic activity was measured as follows: Factor $X_a$ or Factor $II_a$ was diluted with the above-mentioned agents in TBSA. The reaction mixture was stirred with a Teflon-coated stirrer in a plastic dish (37° C.). After 10 minutes, a sample of 100 ul ($X_a$) or 50 ul ($II_a$) was placed in another plastic dish (37° C.) which contained 800 ul of TBSE, 100 ul of TBSA, and 100 ul of S 2337 (2 mM) or 900 ul S 2238 (5 mM). The change in absorption at 405 nM was measured using a Kontron Spectrophotometer Uvikon 810 (37° C.).
The final concentrations of the various agents in the reaction mixtures were as follows: Factor $X_a$ (18.7 nM); Factor $II_a$ (1.5 nM); human AT-III (18.7 nM); heparin (1 unit per ml); and VAC (10.7 ug/ml, specific activity: 1300 units/mg).
[b]N.D. = not determined.

What is claimed as new and intended to be secured by Letters Patent is:

1. A substantially purified anti-coagulant protein obtainable from the walls of mammalian blood vessels and belonging to the group of vascular anti-coagulants which inhibit the coagulation induced by a vascular coagulant or by factor $X_a$, but does not inactivate the coagulation factors, inhibit the biological and amidolytic activity of factors $X_a$ and $II_a$, or inhibit coagulation induced by thrombin.

* * * * *

UNITED STATES PATENT AND TRADEMARK OFFICE
CERTIFICATE OF CORRECTION

PATENT NO. : 5,066,788

DATED : November 19, 1991

INVENTOR(S) : Christian P.M. Reutelingsperger

It is certified that error appears in the above-identified patent and that said Letters Patent is hereby corrected as shown below:

Title page:

The listing for "Inventor:" should read:

--Christian P.M. Reutelingsperger,
      Maastricht, Holland--

The listing for "Related U.S. Application Data" should read:

--Continuation of Ser. No. 123,970, Nov. 23, 1987, which
      is a division of Ser. No. 779,287, Sept. 23, 1985, Pat.
      No. 4,736,018.--

Signed and Sealed this

Twenty-seventh Day of April, 1993

*Attest:*

MICHAEL K. KIRK

*Attesting Officer*      *Acting Commissioner of Patents and Trademarks*